United States Patent
Müller-Rees et al.

(10) Patent No.: US 9,200,247 B2
(45) Date of Patent: *Dec. 1, 2015

(54) BIOREACTOR CONSISTING OF SILICONE MATERIALS

(75) Inventors: Christoph Müller-Rees, Pullach (DE); Rupert Pfaller, Munich (DE)

(73) Assignee: Wacker Chemie AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/389,317

(22) PCT Filed: Aug. 6, 2010

(86) PCT No.: PCT/EP2010/061487
§ 371 (c)(1),
(2), (4) Date: Feb. 7, 2012

(87) PCT Pub. No.: WO2011/015653
PCT Pub. Date: Feb. 10, 2011

(65) Prior Publication Data
US 2012/0135513 A1    May 31, 2012

(30) Foreign Application Priority Data
Aug. 7, 2009    (DE) .......................... 10 2009 028 339

(51) Int. Cl.
*C12M 1/00*    (2006.01)
*C12M 3/00*    (2006.01)
*C12M 1/24*    (2006.01)

(52) U.S. Cl.
CPC ............... *C12M 39/00* (2013.01); *C12M 21/02* (2013.01)

(58) Field of Classification Search
CPC ............................ C12M 21/02; C12M 39/00
USPC ............................................. 435/283.1–309.4
See application file for complete search history.

(56) References Cited

U.S. PATENT DOCUMENTS

| | | | |
|---|---|---|---|
| 3,702,778 | A | 11/1972 | Mueller et al. |
| 6,432,713 | B2 | 8/2002 | Takagi et al. |
| 2001/0021529 | A1 | 9/2001 | Takagi |
| 2003/0073231 | A1 | 4/2003 | Dutil |
| 2004/0050297 | A1* | 3/2004 | Kobayashi et al. ...... 106/287.14 |
| 2004/0210024 | A1 | 10/2004 | Schafer et al. |
| 2004/0254325 | A1 | 12/2004 | Kuepfer et al. |
| 2005/0227092 | A1* | 10/2005 | Yamaya et al. ............... 428/447 |
| 2007/0048848 | A1 | 3/2007 | Sears |
| 2008/0311649 | A1 | 12/2008 | Cloud et al. |
| 2009/0011492 | A1 | 1/2009 | Berzin |
| 2009/0143496 | A1 | 6/2009 | Ziche |
| 2010/0190227 | A1* | 7/2010 | Dauth et al. .................. 435/168 |
| 2011/0020879 | A1 | 1/2011 | Isobe et al. |

FOREIGN PATENT DOCUMENTS

| | | |
|---|---|---|
| CN | 1737107 | 2/2006 |
| DE | 44 16 069 A1 | 10/1995 |
| DE | 198 50 607 A1 | 5/2000 |
| DE | 10 2005 025 118 A1 | 1/2007 |
| DE | 10 2009 029 792 A1 | 12/2010 |
| EP | 1 412 416 B1 | 9/2004 |
| EP | 1 489 129 B1 | 4/2006 |
| GB | 1307001 | 2/1973 |
| GB | 2118572 A | 11/1983 |
| JP | 3-251170 | 11/1991 |
| JP | 2006-349557 | 12/2006 |
| JP | 2007124971 A2 | 5/2007 |
| JP | 2009-60876 | 3/2009 |
| WO | WO 0194487 A2 | 12/2001 |
| WO | 2004/108881 A2 | 12/2004 |
| WO | 2006058656 A2 | 6/2006 |
| WO | 2007/129327 A1 | 11/2007 |
| WO | WO 2008055190 A2 | 5/2008 |
| WO | WO 2008132196 A1 | 11/2008 |
| WO | 2008/145719 A1 | 12/2008 |
| WO | 2009/037683 A1 | 3/2009 |
| WO | WO 2009/091048 A1 | 7/2009 |

OTHER PUBLICATIONS

Winnacker/Küchler, "Chemische Technik: Prozesse und Produkte, vol. 5: Organische Zwischenverbindungen, Polymere", p. 1095-1213, Wiley-VHC Weinheim (2005).
English Abstract corresponding to Winnacker/Küchler, Chemische Technik: Prozesse und Produkte, vol. 5: "Organische Zwischenverbindungen, Polymere", p. 1095-1213, Wiley-VHC Weinheim (2005).
Alvarez, C., International Search Report dated Jan. 27, 2011 for International Application No. PCT/EP2010/061487.
Schumacher et al., James F. "Engineered antifoulding microtopographies—effect of feature size, geometry, and roughness on settlement of zoospores of the green alga Ulva," Biofouling, 2007, 23(1), pp. 55-62.

(Continued)

*Primary Examiner* — Nathan Bowers
*Assistant Examiner* — Lydia Edwards
(74) *Attorney, Agent, or Firm* — RatnerPrestia

(57) ABSTRACT

The invention relates to a bioreactor for cultivating phototrophic organisms in an aqueous culture medium, the reactor parts that come into contact with the culture medium being entirely or partially produced from silicone materials. The invention is characterized in that the silicone materials are produced from addition-crosslinked silicones, and the surface of the silicone materials has a contact angle to the water of at least 100°.

7 Claims, No Drawings

(56) References Cited

OTHER PUBLICATIONS

Shi Hang et al. (2008) Study on New Silicone Marine Anti-fouling Coatings, Silicone Material, vol. 22, issue 6, pp. 339-343 (contains English language abstract).
U.S. Appl. No. 13/389,333 Non-Final Office Action dated Dec. 5, 2012.
U.S. Appl. No. 13,389,333, Response to Non-Final Office Action dated Apr. 5, 2013.
U.S. Appl. No. 13/389,333 Final Office Action dated Jul. 11, 2013.
U.S. Appl. No. 13/389,333, Response to Final Office Action dated Oct. 17, 2013.
U.S. Appl. No. 13/389,333 Advisory Action dated Oct. 30, 2013.
U.S. Appl. No. 13/389,333, Response to Advisory Action dated Dec. 17, 2013.
U.S. Appl. No. 13/389,333 Non Final Office Action mailed Jan. 8, 2014.
Oliveira, R., et al., "The Role of Hydrophobicity in Bacterial Adhesion," Hydrophobicity and Adhesion, BioLine 2001, pp. 11-22.
Final Office Action for U.S. Appl. No. 13/389,333 dated Sep. 26, 2014.

* cited by examiner

BIOREACTOR CONSISTING OF SILICONE MATERIALS

CROSS REFERENCE TO RELATED APPLICATIONS

This application is the national phase filing of international patent application No. PCT/EP2010/061487, filed 6 Aug. 2010, and claims priority of German patent application number 10 2009 028 339.0, filed 7 Aug. 2009, the entireties of which applications are incorporated herein by reference.

FIELD OF THE INVENTION

The invention relates to a bioreactor that is provided with silicones, method of production of bioreactors, and the use of silicones for the production of bioreactors.

BACKGROUND OF THE INVENTION

Bioreactors are used for large-scale industrial production of phototrophic organisms, e.g. cyanobacteria or microalgae, for example *Spirulina, Chlorella, Chlamydomonas* or *Haematococcus*. These microalgae are able, with the aid of light energy, to convert $CO_2$ and water into biomass. Photobioreactors of the first generation use sunlight as the light source. The reactors consist of large open tank units of various shapes, for example round tanks with diameters of up to 45 m and rotating stirring arms. These reactors are generally made of concrete or plastics. Closed bioreactors are also used in many different forms. Closed bioreactors can be plate-type bioreactors, tubular bioreactors, (bubble) column bioreactors or hose-type bioreactors. This type of reactor is made of transparent or translucent materials, such as glass or plastic.

To date, the culture conditions of phototrophic microorganisms, which are produced in closed reactors, cannot be kept constant for an extended period, as the phototrophic microorganisms that form in a culture phase are deposited on the reactor walls, which leads to fluctuations in the amount of light supplied to the culture medium and to variable mixing of the culture medium. Algal deposits are often caused by stress conditions during cultivation, the causes of which can be uncontrolled growth conditions (e.g. light, temperature in open-pond and in closed reactors) of the microorganisms or induction of the production of valuable substances by the phototrophic organisms (e.g. astaxanthin, beta-carotene).

WO 2007/129327 A1 relates to a photobioreactor for cultivation of biomass, which is constructed of transparent, helically-coiled tubes. Silicone is generally recommended as tube material, and there is no discussion of the fouling problem. The illumination of photoreactors with LED plastic moldings is described in WO 2008/145719. Steel, plastics and ceramics are listed as reactor materials. The illuminating element is preferably an LED silicone molding. WO 2004/108881 A2 includes a bioreactor arrangement of vessel and light source, and all possible plastics, including silicones that are not specified in greater detail, are stated as materials for the vessel. WO 2009/037683 A1 describes a bathtub-shaped bioreactor with umbrella-shaped cover made of transparent materials, which are not further specified. Gas-permeable hoses, preferably of silicone, are used for feed of carbon dioxide. GB 2118572 A describes a photobioreactor with glass tubes, which are joined with U-shaped connectors made of silicone. DE 10 2005 025 118 A1 describes a photobioreactor made of glass tubes, wherein microorganisms that have accumulated on surfaces are removed by means of ultrasound. US 2003/0073231 A1 describes a photobioreactor made of thermoplastics such as polyvinyl chloride or polyethylene. The object of US 2007/0048848 A1 is also a photobioreactor made from thermoplastics. In both cases, deposits of microorganisms on the reactor walls are removed by mechanical means, for example brushing. These are in all cases relatively expensive methods, which cannot be scaled up as desired. In DE 44 16 069 A1 it is recommended to provide light-conducting fibers, which are used for illuminating bioreactors, with a smooth surface. US 2008/0311649 A1 proposes increasing the flow rate of the medium containing the algae in tubular bioreactors, to prevent deposition of the algae. This has the disadvantage that the culture parameters with respect to flow rate can no longer be set independently.

SUMMARY OF THE INVENTION

Against this background, the problem to be solved was to improve bioreactors for cultivation of microorganisms, so that fouling with microorganisms on the reactor parts coming into contact with the culture medium is largely prevented, and any fouling that does occur can be removed inexpensively. The solution should not have a negative effect on product quality, it should be up-scalable, and should be capable of universal application, independently of the process parameters required for cultivation.

The invention relates to a bioreactor for the cultivation of phototrophic organisms in an aqueous culture medium, in which reactor parts coming into contact with the culture medium are made completely or partially from silicone materials, characterized in that the silicone materials are made from addition-crosslinked silicones, and the surface of the silicone materials has a contact angle with water of at least 100°.

DETAILED DESCRIPTION OF THE INVENTION

Organisms suitable for cultivation are in particular phototrophic macro- or microorganisms. Phototrophic organisms are designated as those that require light and carbon dioxide, or optionally another carbon source as well, for growth. Examples of phototrophic macroorganisms are macroalgae, plants, mosses, plant cell cultures. Examples of phototrophic microorganisms are phototrophic bacteria such as purple bacteria and phototrophic microalgae including cyanobacteria. Preferably the bioreactor is used for the cultivation of phototrophic microorganisms, especially preferably the cultivation of phototrophic microalgae.

The bioreactor can be a closed reactor or an open reactor, in each case of any desired shape. For example, in the case of open reactors it is possible to use tanks or so-called "open ponds" or "raceway ponds". Closed reactors are preferred as bioreactors. The closed bioreactors can be for example plate-type bioreactors, tubular bioreactors, (bubble) column bioreactors or hose-type bioreactors. Plate-type bioreactors consist of perpendicular or slanting brick-shaped plates, with a large number of plates joined together to form a quite large reactor system. Tubular bioreactors consist of a tube system, which can be arranged vertically or horizontally or at any angle in between, and the tube system can be very long, preferably up to several hundred kilometers. The culture medium is then transported through the tube system, preferably by means of pumps or by the air-lift principle. The column bioreactor consists of a closed, cylindrical vessel, which is filled with the culture medium. In bioreactors of this type, carbon dioxide is introduced, and the ascending bubble column provides mixing of the culture medium. Hose-type reactors comprise a reactor system that consists of a single hose of any length or a large number of hoses of any length, preferably of hoses up to several meters long.

The bioreactors are preferably made of transparent or translucent, addition-crosslinked silicone materials. Transparent silicone materials are to be understood as those that let through at least 80% of the light in the spectral range from 400 nm to 1000 nm. Translucent silicone materials are to be understood as those that let through at least 50% of the light in the spectral range from 400 nm to 1000 nm. Reactor parts mean the reactor walls including reactor bottom and reactor cover and structure-forming elements in the culture medium, for example baffles. In the case of tubular, plate-type and hose-type reactors, the tubes, plates and hoses correspond to the reactor walls. The reactor walls are preferably made completely or partially of silicones. Especially preferably, in the case of tubular reactors or plate-type reactors, the tubes or plates are made of addition-crosslinked silicones. In the case of column reactors, the cylindrical vessels are made of addition-crosslinked silicones.

Suitable silicones for the production of bioreactors are addition-crosslinking silicones, wherein the addition crosslinking can be initiated thermally or by means of radiation. Peroxide-crosslinked silicones have the disadvantage that these silicones have greater stickiness in the crosslinked state than addition-crosslinked silicones.

Addition-crosslinking silicone rubber systems contain
a) organosilicon compounds, which have residues with aliphatic carbon-carbon multiple bonds,
b) optionally organosilicon compounds with Si-bound hydrogen atoms or instead of a) and b)
c) organosilicon compounds, which have residues with aliphatic carbon-carbon multiple bonds and Si-bound hydrogen atoms,
d) catalysts promoting the addition of Si-bound hydrogen on aliphatic multiple bonds and
e) optionally agents delaying the addition of Si-bound hydrogen on aliphatic multiple bonds at room temperature.

Suitable silicone rubbers crosslinking by an addition reaction are high-temperature vulcanizing (HTV) solid silicone rubbers.

Addition-crosslinked HTV silicone rubbers are obtained by crosslinking of organopolysiloxanes multiply substituted with ethylenically unsaturated groups, preferably vinyl groups, with organopolysiloxanes multiply substituted with Si—H groups in the presence of platinum catalysts.

Preferably one of the components of the addition-crosslinking HTV-2 silicone rubbers consists of dialkylpolysiloxanes of structure $R_3SiO[—SiR_2O]_n—SiR_3$ with $n \geq 0$, generally with 1 to 4 carbon atoms in the alkyl residue R, wherein the alkyl residues can be replaced completely or partially with aryl residues such as the phenyl residue and at one or at both ends one of the terminal residues R is replaced with a polymerizable group such as the vinyl group. However, polymers with side or with side and terminal vinyl groups can also be used. Preferably vinyl end-blocked polydimethylsiloxanes of structure $CH_2=CH_2—R_2SiO[—SiR_2O]_n—SiR_2—CH_2=CH_2$ are used, and vinyl end-blocked polydimethylsiloxanes of the aforesaid structure, which also bear vinyl side groups. In the case of addition-crosslinking HTV silicone rubbers, the second component is a copolymer of dialkylpolysiloxanes and polyalkylhydrogensiloxanes with the general formula $R'_3SiO[—SiR_2O]_n—[SiHRO]_m—SiR'_3$ with $m \geq 0$, $n \geq 0$ and R with the meaning given above and with the proviso that at least two SiH groups must be contained, wherein R' can have the meaning of H or R. There are accordingly crosslinking agents with side and terminal SiH groups, whereas siloxanes with R'=H, which only have terminal SiH groups, can also still be used for chain extension. Platinum catalysts can be used as crosslinking catalysts. HTV silicone rubbers are also processed as a one-component system.

Other suitable materials are crosslinked silicone hybrid materials, as described in WO 2006/058656, the relevant information of which is incorporated by reference in this application.

A detailed review of silicones, their chemistry, formulation and application properties is given for example in Winnacker/Küchler, "Chemische Technik: Prozesse and Produkte, Vol. 5: Organische Zwischenverbindungen, Polymere", p. 1095-1213, Wiley-VCH Weinheim (2005).

The surface morphology of the silicone moldings is important for the inhibition or prevention of fouling with microorganisms. The surface morphology is determined from the contact angle of said surface with water. The contact angle according to the invention is adjusted by selection of the silicone materials according to the invention. Further measures for increasing the contact angle, for example roughening of the surface (e.g. simulation of the so-called lotus effect), are preferably ignored. In fact such roughening can disturb the cultivation of phototrophic microorganisms. Surfaces with contact angles between 100° and 120° are preferred, surfaces with contact angles between 100° and 115° are especially preferred, and surfaces with contact angles between 100° and 113° are quite especially preferred. The contact angle of the surface of the silicone moldings with water can be determined by methods known by a person skilled in the art, for example according to DIN 55660-2, using commercially available measuring instruments for determining the contact angle, for example the contact angle measuring systems obtainable from the company Krüss.

Optionally the addition-crosslinked silicones can contain usual additives for promoting adhesion or usual fillers or fiber materials for improving the mechanical properties. These additives are preferably used in maximum amounts such that the silicone molding remains transparent or translucent. Light-conducting additives and light wave-displacing additives can also be added.

The reactor parts coming into contact with the culture medium, in particular the reactor walls, are made at least partially, preferably completely, from the aforementioned addition-crosslinked silicones. Manufacture can take place with the established technologies for plastics processing, which are used for the production of molded bodies such as plates, hoses, tubes or containers of any shape; for example by means of extrusion for making plates, tubes, hoses, or injection molding.

Laminates can also be produced, which consist of a composite of an addition-crosslinked silicone molding and of a glass or plastic molding, i.e. a laminate with materials that have been used until now for the production of bioreactors. Examples of conventional materials for bioreactors are glass or plastics such as polymethyl methacrylate (Plexiglas), polyesters such as PET, polycarbonate, polyamide, polystyrene, polyethylene, polypropylene, polyvinyl chloride. With these laminates, it is possible to make bioreactors whose interior, i.e. the side facing the cultivation medium, consists of addition-crosslinked silicone.

The bioreactors are equipped with reactor fittings; for example, for filling and supply of nutrients, with feed lines and, for product separation and emptying, with discharge lines (e.g. for salt and feed solutions). For cooling and heating, the bioreactors can optionally be equipped with heating and cooling devices such as heat exchangers. Moreover, the bioreactors can also contain stirring devices and pumps for mixing. Bioreactors are often also equipped with devices for artificial illumination. Further examples of reactor devices are measuring and control instruments for monitoring operation (e.g. analysis of pH, $O_2$, $CO_2$, ion conductivity, luminous intensity). In a preferred embodiment the reactor fittings are also coated completely or partially with silicone.

The photobioreactors made from addition-crosslinking silicone moldings, with surfaces with a contact angle with water with values of at least 100°, minimize the deposition of the phototrophic organisms that form, so that the flow conditions of the culture medium remain constant, and the light input that is ideal for growth remains set at optimal growth. The surface finish of the silicone moldings according to the invention with a contact angle with water of at least 100° on the one hand reduces the accumulation of water on the silicone surface, and on the other hand substances dissolved in water, which for example arise through stress situations during cultivation of the algae, are kept away from the surface.

Moreover, expenditure on cleaning between individual cultivation cycles and on changing the phototropic organisms to be cultivated is minimized. Any organisms adhering to the coated surfaces can be removed between the cultivation cycles by spraying with a cleaning agent for example with water, ethanol or $H_2O_2$ without further mechanical treatment. This leads to substantial economic advantages on account of shorter downtime and lower cleaning costs. Another advantage is the high UV-stability of addition-crosslinked silicones with the surface finish according to the invention, which, especially in an outdoor setting, greatly increases the service life of bioreactors made of addition-crosslinked silicone materials with the surface finish according to the invention compared with bioreactors made from conventional plastics.

The invention claimed is:

1. A bioreactor for the cultivation of photrophic organisms, said bioreactor comprising an aqueous culture medium of a phototropic organism and reactor walls coming into contact with the culture medium, wherein the reactor walls completely or partially comprise silicone materials, wherein the silicone materials comprise addition-crosslinked silicones, wherein the surface of the silicone materials has a contact angle with water of at least 100°, and wherein the surface of the silicone materials largely prevents biofouling on the reactor parts coming into contact with the culture medium during the cultivation of the phototropic organisms.

2. The bioreactor as claimed in claim 1, wherein the bioreactor is a closed reactor.

3. The bioreactor as claimed in claim 1, wherein the bioreactor is a plate bioreactor, tubular bioreactor, bubble column bioreactor or hose bioreactor.

4. The bioreactor as claimed in claim 1, wherein the reactor walls are made of one or more silicones from the group containing addition-crosslinked silicones and addition-crosslinked silicone hybrid polymers.

5. The bioreactor as claimed in claim 1, wherein the reactor walls are made of one or more silicones selected from the group consisting of addition-crosslinked HTV silicone rubbers and addition-crosslinked silicone hybrid polymers.

6. A method of producing a bioreactor for the cultivation of phototropic organisms, comprising the steps of providing one or more reactor walls containing an aqueous culture medium of a phototropic organism, wherein the reactor walls coming into contact with the culture medium completely or partially comprise addition-crosslinked silicone materials, the surfaces of which have a contact angle with water of at least 100°, and wherein the surfaces largely prevent biofouling on the reactor parts coming into contact with the culture medium during the cultivation of the phototropic organisms.

7. A method of producing a bioreactor for the cultivation of phototropic organisms, comprising the steps of forming by extrusion, injection molding, or lamination one or more reactor walls for containing an aqueous culture medium of a phototropic organism, wherein the reactor walls comprise addition-crosslinked silicones, and wherein the addition-linked silicones form a layer, the surface of which has a contact angle with water of at least 100° and largely prevents biofouling on the reactor parts coming into contact with the culture medium during the cultivation of the phototropic organisms.

* * * * *